US008128230B2

(12) United States Patent
Zuccolotto et al.

(10) Patent No.: US 8,128,230 B2
(45) Date of Patent: *Mar. 6, 2012

(54) SYSTEM AND APPARATUS FOR OBJECT BASED ATTENTION TRACKING IN A VIRTUAL ENVIRONMENT

(75) Inventors: Anthony P Zuccolotto, Freeport, PA (US); Thomas J Yothers, Turtle Creek, PA (US); Kyle D Brauch, Pittsburgh, PA (US)

(73) Assignee: Psychology Software Tools, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/855,948

(22) Filed: Aug. 13, 2010

(65) Prior Publication Data

US 2011/0063570 A1    Mar. 17, 2011

Related U.S. Application Data

(63) Continuation of application No. 12/140,229, filed on Jun. 16, 2008, now Pat. No. 7,775,661.

(60) Provisional application No. 60/944,094, filed on Jun. 14, 2007.

(51) Int. Cl.
*A61B 3/14* (2006.01)
*A61B 3/00* (2006.01)

(52) U.S. Cl. .................. 351/209; 351/210; 351/246
(58) Field of Classification Search .......... 351/200–246
See application file for complete search history.

(56) References Cited

U.S. PATENT DOCUMENTS

| 5,015,083 A * | 5/1991 | Wurst et al. ............... 359/630 |
| 7,549,743 B2 * | 6/2009 | Huxlin et al. ............. 351/203 |
| 7,775,661 B2 * | 8/2010 | Zuccolotto et al. ....... 351/209 |

* cited by examiner

*Primary Examiner* — Mohammed Hasan
(74) *Attorney, Agent, or Firm* — Blynn L. Shideler; Krisanne Shideler; BLK Law Group

(57) ABSTRACT

A system and operational method that supplies visual stimuli to each subject in the form of a virtual environment in which at least the objects of interest have a three dimensional wire frame or mesh frame of a number of polygons that is surrounded with at least one skin or surface; wherein the visual stimuli is presented in a test session to the subject on a display device including an eye tracking sub-system that can effectively track the subject's gaze direction and focus on the display device throughout the test session; wherein unique colors are assigned to the mesh frame and/or an eye tracking skin of each object of interest whereby the system can evaluate the obtained eye tracking data and assign attention data to specific objects of interest resulting in object specific attention data.

20 Claims, 9 Drawing Sheets

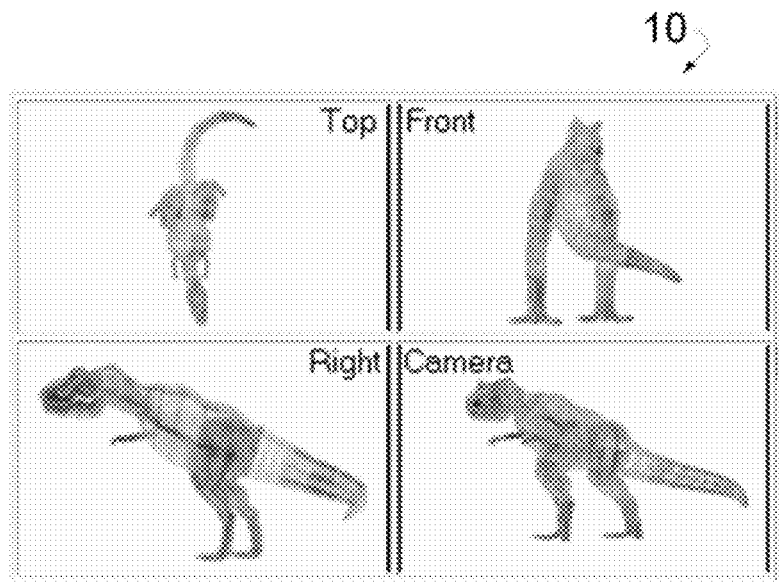
FIG. 4
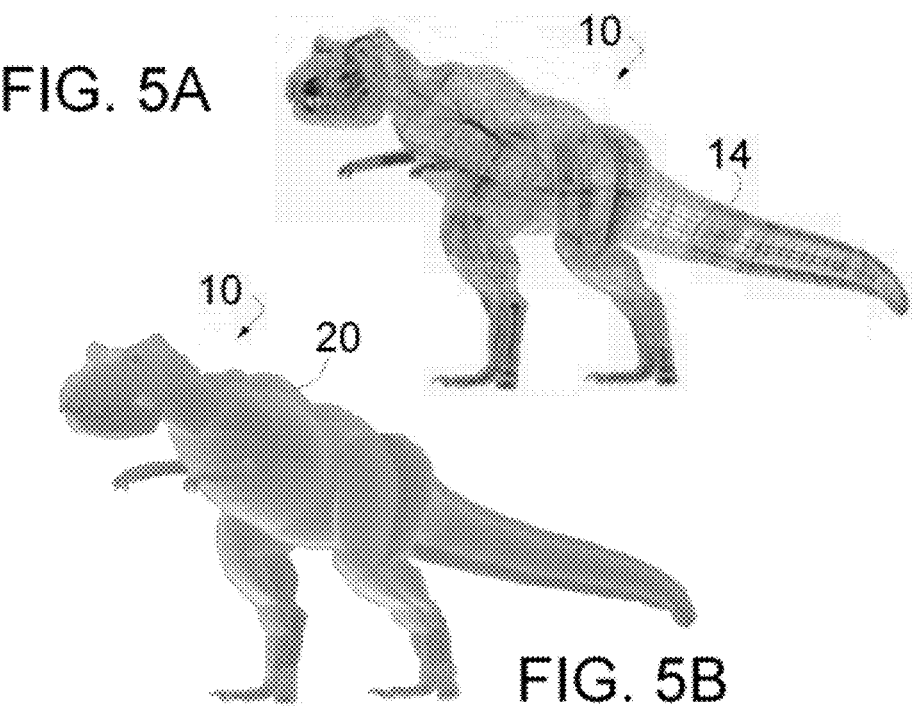
FIG. 5A
FIG. 5B

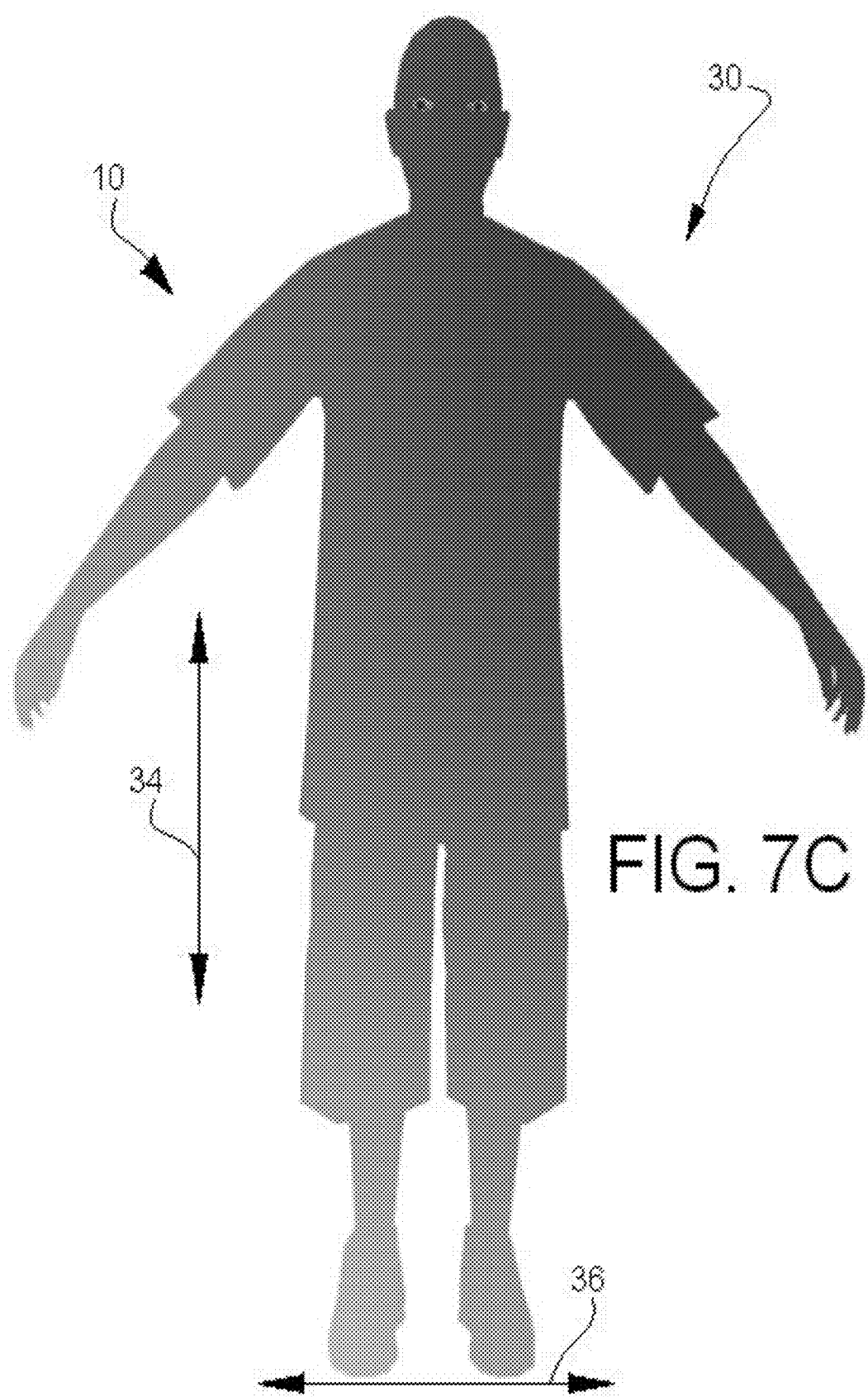

US 8,128,230 B2

SYSTEM AND APPARATUS FOR OBJECT BASED ATTENTION TRACKING IN A VIRTUAL ENVIRONMENT

RELATED APPLICATION

The present application is a continuation of U.S. patent application Ser. No. 12/140,229 filed Jun. 16, 2008, now U.S. Pat. No. 7,775,661, which is incorporated herein by reference. U.S. patent application Ser. No. 12/140,229 claims the benefit of provisional patent application 60/944,094 filed Jun. 14, 2007.

BACKGROUND OF THE INVENTION

1. Field of the Invention

The present invention relates to object based attention tracking in a virtual environment.

2. Background Information

Eye-tracking within this application will reference the point of gaze of a subject, rather than associating the motion of the eye relative to the head that is also referenced as eye tracking (although these two eye tracking items are clearly related).

Eye-tracking has been used in "usability testing" for many years, possibly the first practical applications with cockpit design testing in 1950. Such early work has been valuable in establishing some assumptions about the relationships between eye-movement data and the cognitive activity of a user. Frequency of fixations was assumed to be related to the importance of the control, while the duration of fixations was related with ease of interpreting information.

Alfred L. Yarbus (sometimes spelled Iarbus) was a Russian psychologist who studied eye movements in the 1950s and 1960s and noted "records of eye movements show that the observer's attention is usually held only by certain elements of the picture. ( . . . ) Eye movements reflect the human thought processes; so the observer's thought may be followed to some extent from records of eye movements (the thought accompanying the examination of the particular object). It is easy to determine from these records which elements attract the observer's eye (and, consequently, his thought), in what order, and how often." See A. L. Yarbus, *Eye Movements and Vision*. New York: Plenum Press, 1967. (Translated from Russian by Basil Haigh. Original Russian edition published in Moscow in 1965).

Eye tracking methodologies have been exploited successfully by the print advertising media for several decades. Understanding where a viewer's attention will be directed on static image has been utilized to maximize the effectiveness of the static image, e.g. printed, advertisement. This is merely one use of attention tracking developments which is on the commercial side. Other research applications have been pursued in this field.

The advent of effective computer monitor based eye tracking systems, such as the Tobii T/X™ series of eye trackers from Tobii Technology AB, have significantly improved the abilities of attention tracking review of static images on a computer. Such eye tracking testing provides unique methods to assess the impact of advertisements and web pages. It is believed that where people look accurately reflects their attention, thinking and what information they are processing. Automated eye tracking provides insights that cannot be obtained directly with other testing methods.

It is asserted that by effectively testing a proposed design (such as a print advertisement, product design, or webpage) before launch with an automated eye tracking system, the users are able to greatly improve its impact and avoid large spending on suboptimal design. In contrast to many design testing systems today, such as focus group studies, automatic eye tracking provides objective results. It is asserted that by observing people's eye gaze, a true measure of responses and reactions is obtained without the filtering of the respondent's logical mind or the influence and interpretation of a test leader. It is asserted that such automatic eye tracking provides both qualitative and quantitative results that allow users to gain clear insight and effectively communicate design implications: for example a user can (i) Observe how a subject's eyes wander across a design, in real time or after testing, to obtain a deep and direct understanding of reactions and cognitive thought processes; (ii) Show visualizations like gaze plots and hot spots to effectively illustrate how individuals or groups of people look at a user's design and where to place valuable content, and (iii) quantifiably identify and back up conclusions about what people see and for how long.

As a representative examples of the objective results of typical automatic eye tracking studies, FIG. 1 illustrates a prospective gaze plot 4 of a print advertisement, or static image 2, obtained from and automatic eye tracking study and FIG. 2 is a graph 6 associated with this print advertisement review. FIG. 3 is a hotspot plot 8, also called heat plot, of a collection of subject studies of a prospective webpage or static image 2. These representative illustrations may be found at www.tobii.com along with further descriptions of the abilities of automatic eye tracking for static images 2. Within the meaning of this application eye tracking data, gaze data, hotspot, gaze plots and the like will be collectively referred to as attention tracking or attention data.

Similar automatic eye tracking systems have been applied to video streams as well. The systems work very well at tracking what portions of the screen or monitor the subjects were looking at any given time throughout the session. However, unlike the still images, this data cannot be easily associated with particular three dimensional objects or areas of interest (AOI) within the video stream. In most videos, by their nature, the three dimensional objects move around relative to one another on the monitor.

Some attempts have been made to co-ordinate the eye tracking data of a video stream with the particular three dimensional objects of the video through a laborious hand mapping procedure. In such a mapping procedure the eye tracked data is reviewed in a frame by frame manner and the gaze data is then assigned on a frame by frame basis to specific objects within the video. This process is extremely time consuming so as to make large data samples impractical, further it introduces the subjective issues of the person assigning the gaze data to an object. For example, two different researchers analyzing the same frame may assign the same data differently to two separate objects, e.g. one assigns the data to the face of a person in the foreground and the other assigns the gaze to an automobile in the background of that frame.

There is a need for efficiently, effectively and objectively assigning eye tracking data to moving objects in viewed stimuli. The ability to provide such a tool to researchers and the like will open the door to a greater number of applications than used with still images, as we live in a moving three dimensional world.

SUMMARY OF THE INVENTION

One embodiment of the present invention provides a system and operational method that supplies visual stimuli to each subject in the form of a virtual environment in which at least the objects of interest have a three dimensional wire frame, or mesh frame, of a number of polygons that is surrounded with at least one skin, or surface; wherein the visual stimuli is presented in a test session to the subject on a display device including an eye tracking sub-system that can effectively track the subjects gaze direction and focus on the display device throughout the test session; wherein unique colors are assigned to the mesh frame and/or an eye tracking skin of each object of interest whereby the system can evaluate the obtained eye tracking data and assign attention data to specific objects of interest resulting in object specific attention data.

In one non-limiting embodiment of the present invention the objects of interest have a first realistic skin that is provided on the objects throughout the subject's session, and the session data is evaluated with a second eye tracking skin that is applied to the objects of interest.

In one non-limiting embodiment of the present invention the second skin of at least one object is divided into sub-objects or object parts, with each object part provided with a unique color designation.

In one non-limiting embodiment of the present invention the second skin of at least one object is formed as a wash or range of a given color from one end of the object to the other.

In one non-limiting embodiment of the present invention the second skin of at least one object is formed as a combination of two or three colors with each color being a wash or range of a given color from one end of the object to the other in a given direction and wherein the directions for each color wash are angled with respect to each other.

In one non-limiting embodiment of the present invention the objects of interest are assigned metadata that allows for sorting and categorizing the resulting object attention data.

In one non-limiting embodiment of the present invention the evaluation of the obtained eye tracking data and the assigning of attention data to specific objects of interest that results in object specific attention data is obtained during the session.

In one non-limiting embodiment of the present invention the evaluation of the obtained eye tracking data and the assigning of attention data to specific objects of interest that results in object specific attention data is obtained following the session in post session processing.

In one non-limiting embodiment of the present invention the objects of interest have a first realistic skin that is provided on the objects throughout the subject's session, and the unique colors are assigned to the mesh frame to provide for real time in session object attention data.

In one non-limiting embodiment of the present invention and the session data is evaluated with the combination of unique colors that are assigned to the mesh frame and a second eye tracking skin that is applied to the objects of interest. The assignment of the unique colors may be subsequent to the initial session and can be applied and reapplied as desired to obtain any set or subset of object information in the session.

These and other advantages of the present invention will be clarified in the brief description of the preferred embodiment taken together with the drawings in which like reference numerals represent like elements throughout.

BRIEF DESCRIPTION OF THE DRAWINGS

FIG. 4 is a collection of views of a three dimensional wire frame model of an object, namely a dinosaur, for a virtual environment;

FIG. 5A is a perspective view of the wire frame model of FIG. 4;

FIG. 5B is a perspective view of the wire frame model of FIG. 5A with a overlaying texture or skin;

FIGS. 7C-E are perspective views of the wire frame model of FIG. 7A with an overlaying attention tracking texture or skin in accordance with the objects of the present invention.

DESCRIPTION OF THE PREFERRED EMBODIMENTS

As noted above the objects of the present invention is for efficiently, effectively and objectively assigning eye tracking data to moving objects 10 in viewed stimuli. In addressing this problem the inventors have considered the advantages of computer animation, and namely 3D animation.

Figure 1:
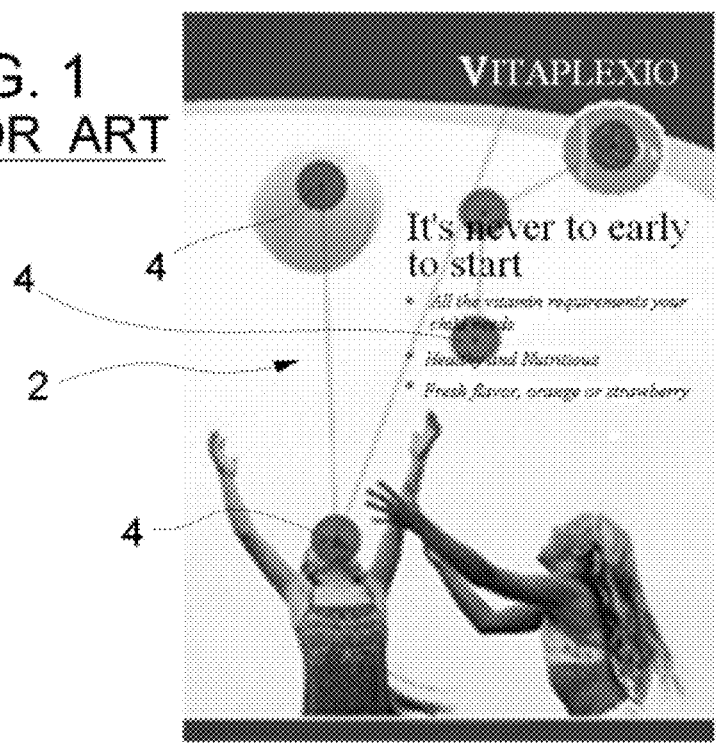
FIG. 1 illustrates a prospective gaze plot of a print advertisement obtained from an automatic eye tracking study with an existing eye tracking system.
Figure 2:
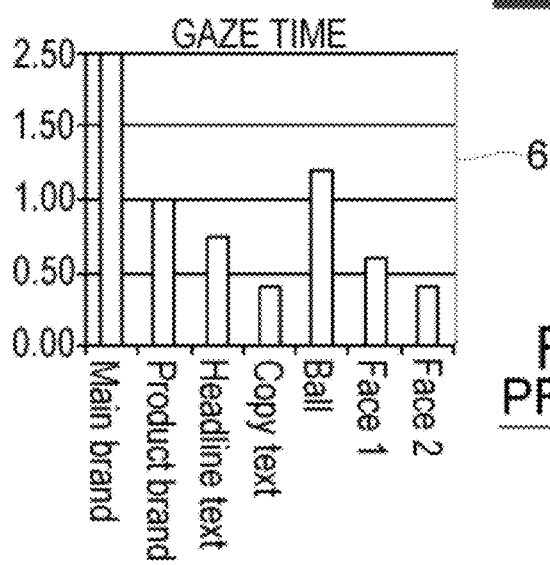
FIG. 2 is a graph associated with the review of FIG. 1.
Figure 3:
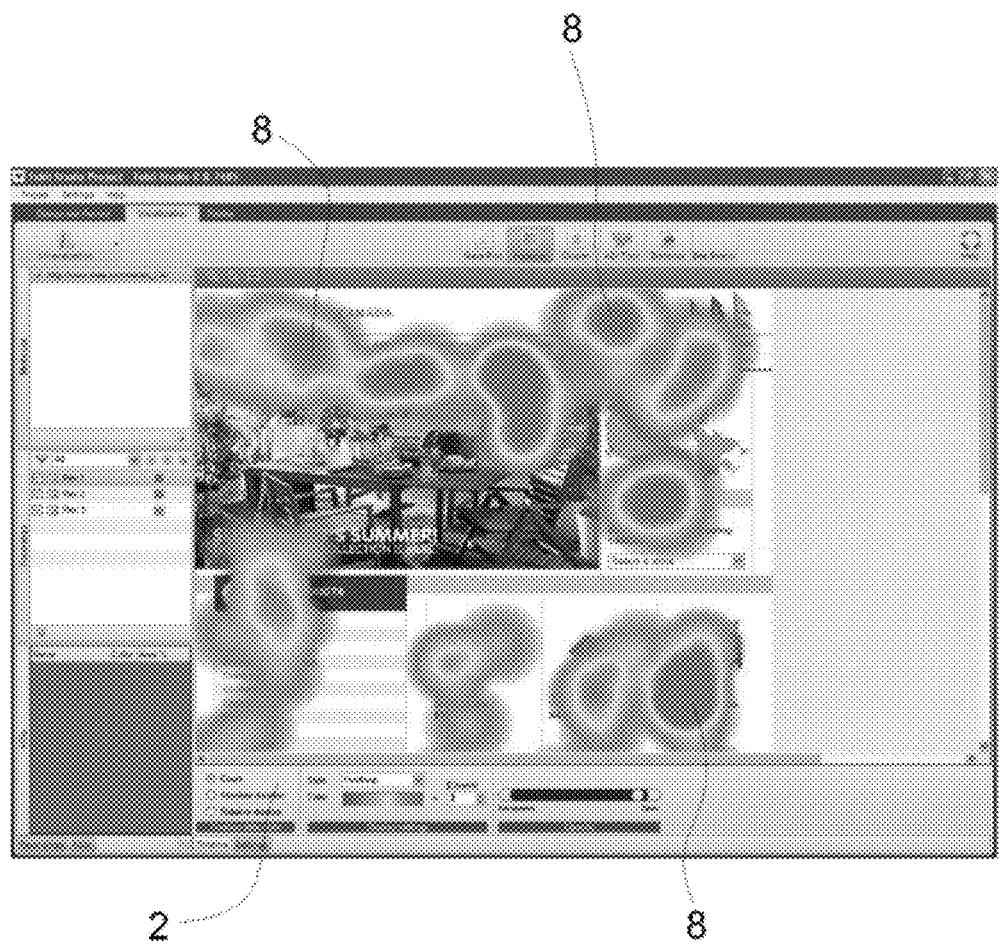
FIG. 3 is a hotspot plot, also called heat plot, of a collection of subject studies of a prospective webpage obtained from an automatic eye tracking study with an existing eye tracking system.
Figure 6A:
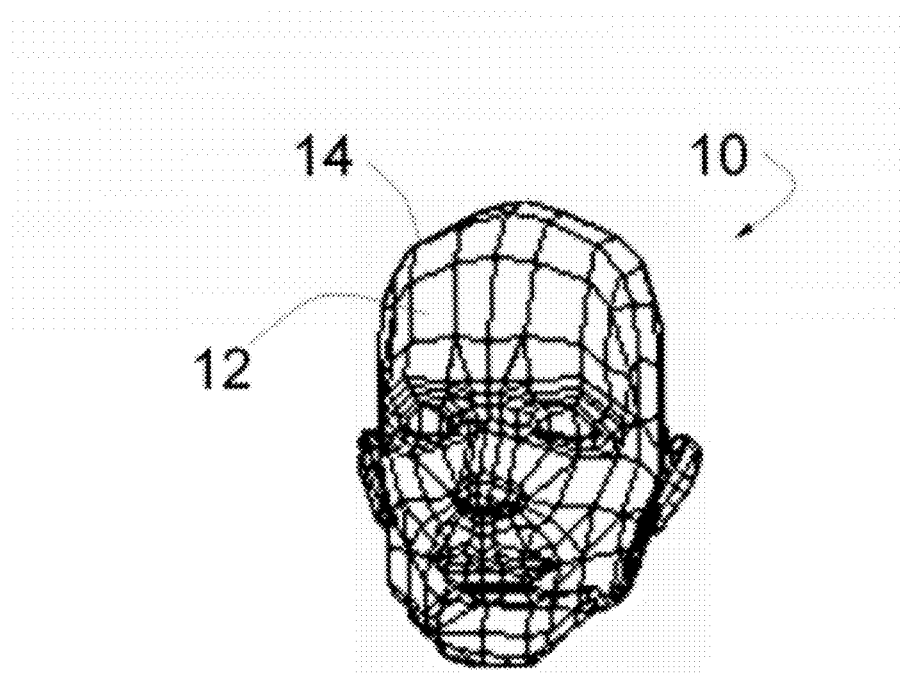
FIG. 6A is a perspective view of a wire frame model of a human head object for a virtual environment.
Figure 6B:
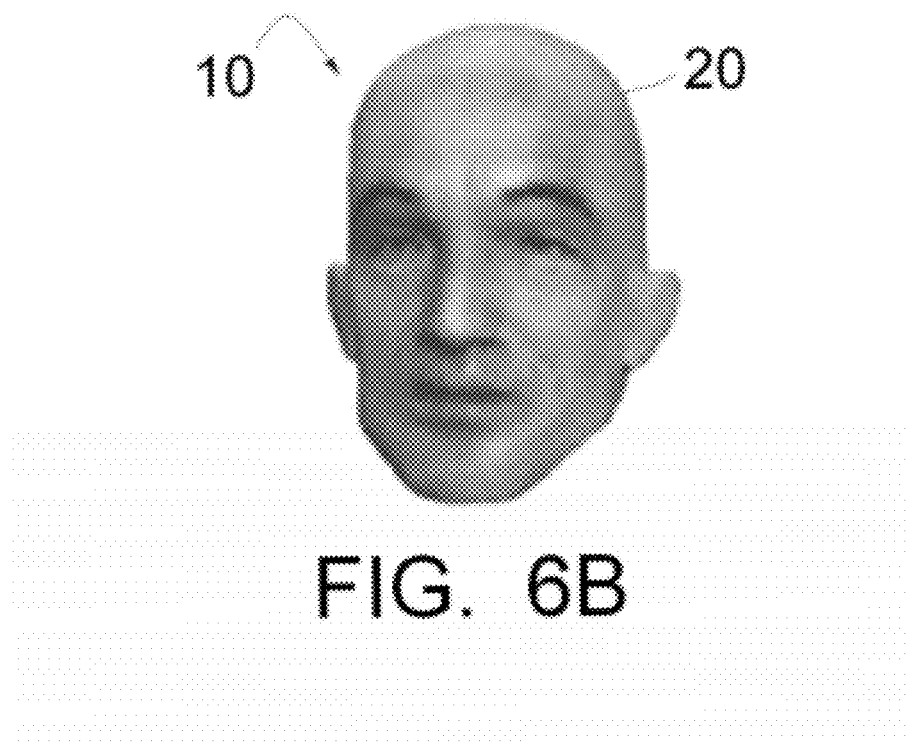
FIG. 6B is a perspective view of the wire frame model of FIG. 6A with an overlaying texture or skin.
Figure 7A:
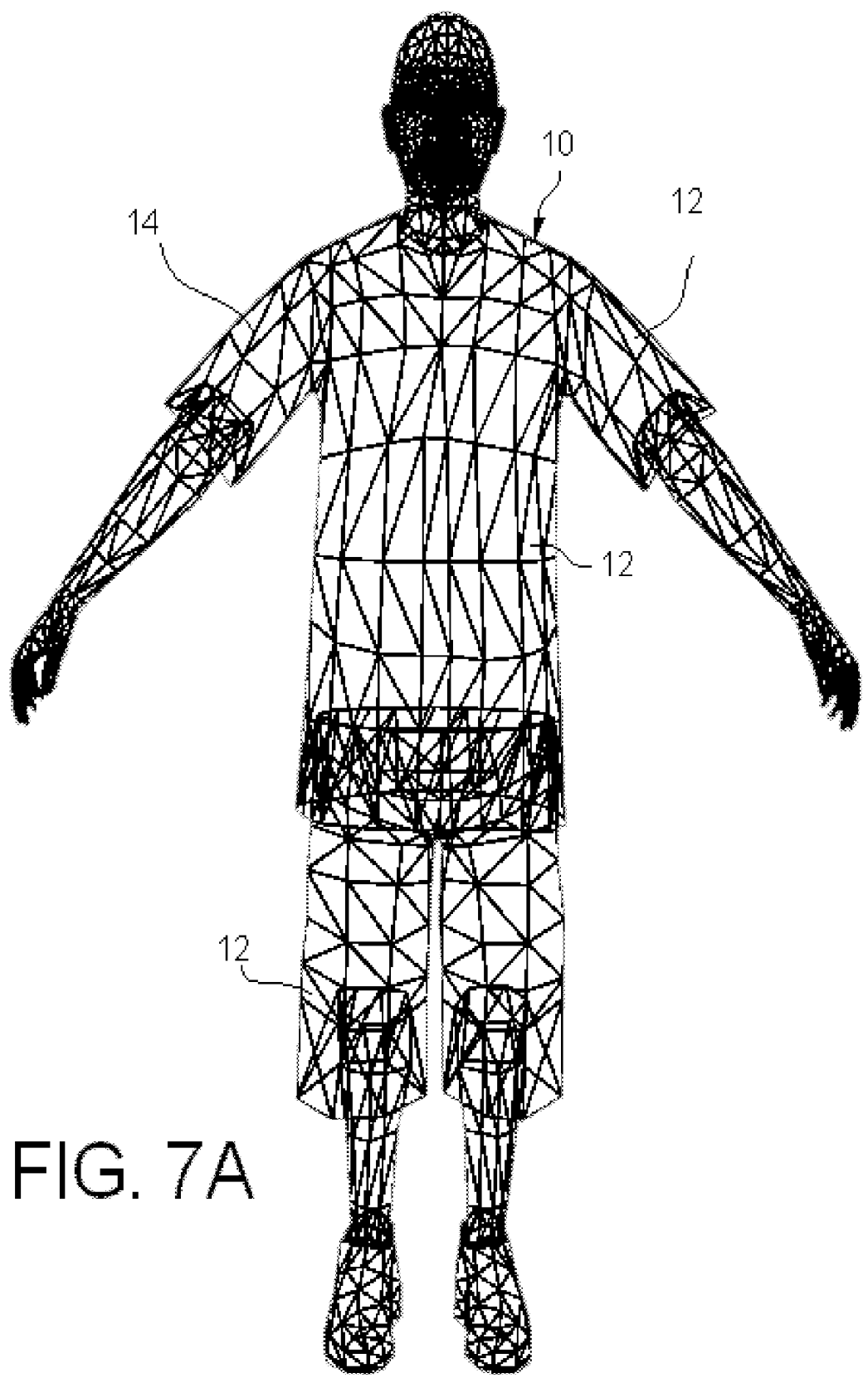
FIG. 7A is a perspective view of a wire frame model of a human head object for a virtual environment.
Figure 7B:
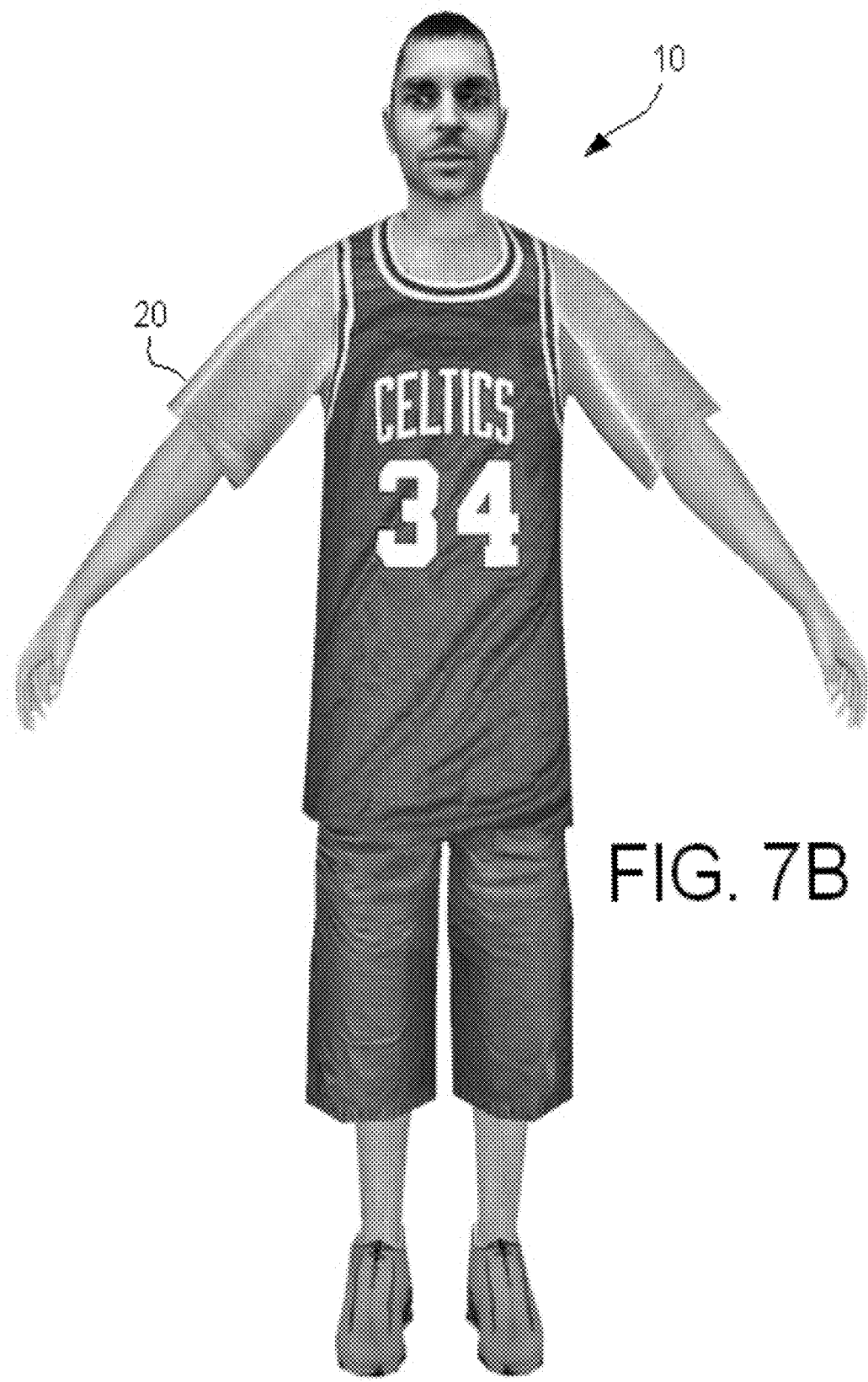
FIG. 7B is a perspective view of the wire frame model of FIG. 7A with an overlaying texture or skin.
Figure 7D:
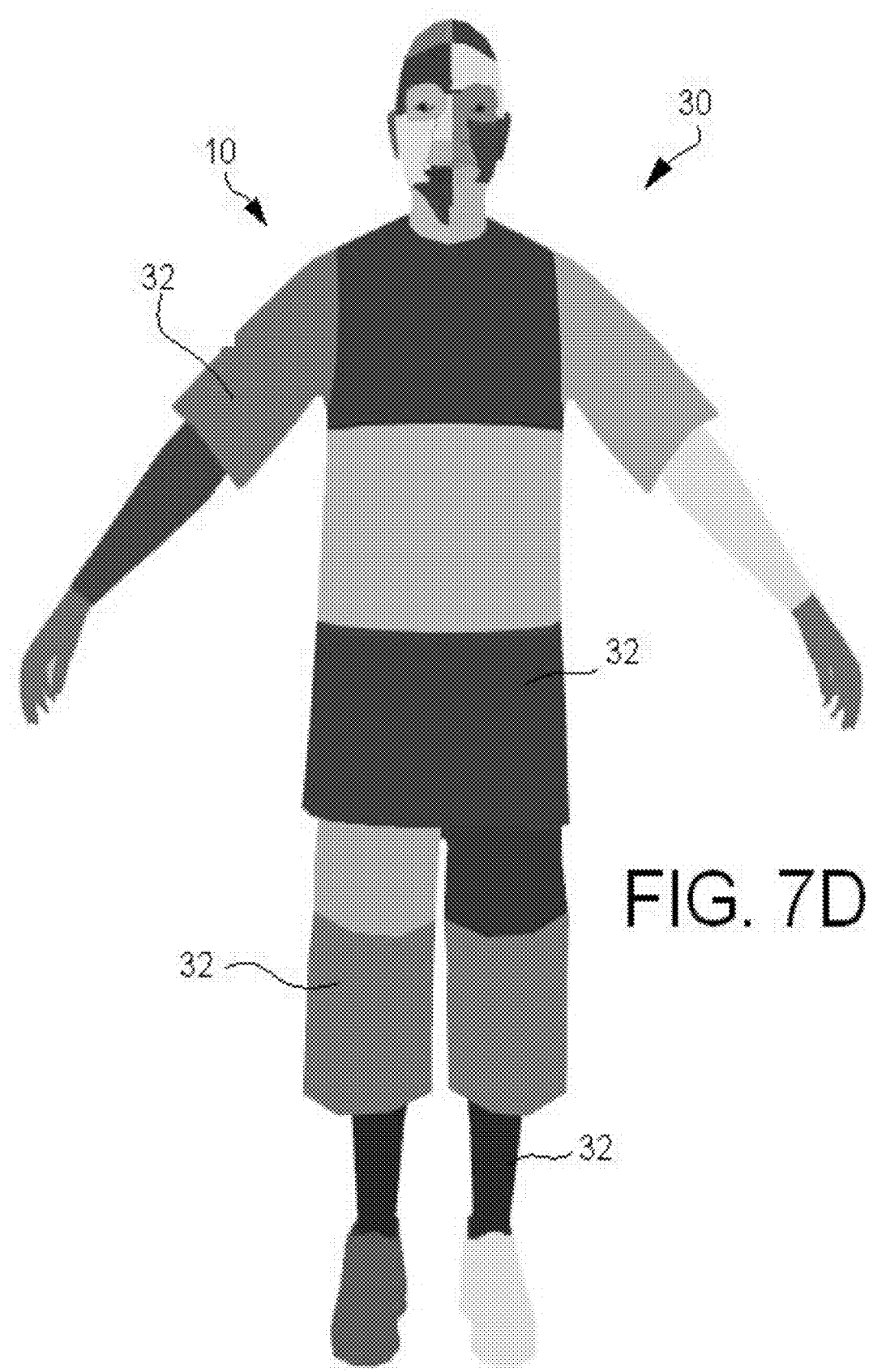
Figure 7E:
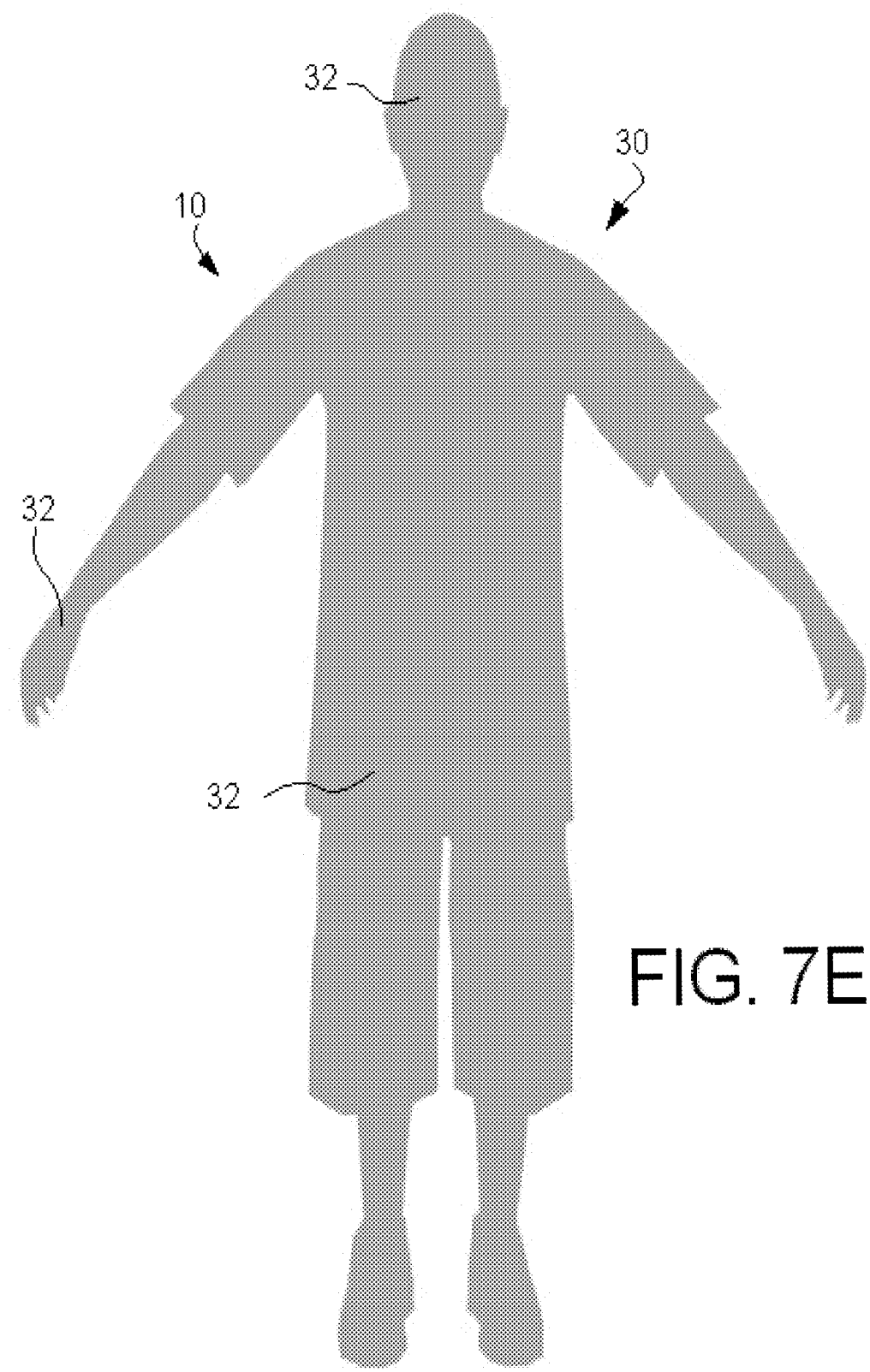

Computer animation can be broadly classified into 2D and 3D animation. Though both categories take the same approach towards animation, the way each still picture is drawn is drastically different. In 2D animation, the artist draws the scene pretty much the same way he would on a sheet of paper. Only instead of using a pencil or a brush, he/she now uses a mouse or a graphic tablet. On the other hand, in 3D animation, every object 10 in the scene is sculpted in 3D to form what is called a wire frame model as shown in FIGS. 4, 5A, 6A and 7A. A wire frame model is actually made up of a series of perpendicular lines 14 following the contours of the object 10, with the lines 14 forming polygons 12 that form the image of the three dimensional object 10. It is the vertices of the lines 14, or corners of the polygons 12, that the computer controls for properly manipulating and drawing the underlying model of the object 10.

FIGS. 4, 5A, 6A and 7A illustrate some wire frame models for objects 10 in 3D animation. A realistic skin 20, or surface texturing, is placed on each model to complete the animation process. Typically the skin 20 adds the detail and realism that allows for extremely rich virtual environments that are common in modern video games and virtual simulations. Shading and lighting considerations are also important for realistic portrayals of objects 10 in virtual environments but such issues do not play an important aspect of the present invention.

It is an important aspect of the present invention that the skins of objects 10 can be readily and easily changed without changing the underlying frame model of an object 10, or altering the eye tracking data collected from the subject.

In computing, a game engine is the core software component of a video game and it typically handles image rendering, on a portion of the game engine sometimes called a renderer, and other necessary technology. The renderer component of the game engine is what performs the 3D animation. The present invention is implemented on existing game engines that utilize this 3D animation technology, such as the Source™ game engine from Valve Corporation that has developed the popular Half-Life 2™ brand video game.

It is important for the system to maintain a history of the eye tracking data collected as discussed below, and of the specific visual stimuli, namely objects 10, presented to the subject in the virtual environment. This record must include what is displayed to the subject, as well as what interactions the subject made with the world, if any (some virtual environments may allow for viewing only with no subject interaction—which is just viewed as a simplified case). This is common in many video games that allow for an "instant replay" of a segment of the game The present invention provides a system and operational method that supplies visual stimuli to each subject in the form of a virtual environment in which at least the three dimensional objects 10 of interest have a three dimensional wire frame or mesh frame of a number of polygons 12 that is surrounded with at least one skin 20 or surface. The creation of a virtual environment is certainly well known to those in the gaming arts and familiar with 3D wire frame modeling.

The movement and operation of the various simulated objects 10 within the virtual environment will also be well known to those in the gaming arts. For example, some gaming engines have an excellent representation of gravity and acceleration so that objects realistically move in a given environment in accordance with conventional physics.

Further, it is well known to create a virtual environment that the user interacts with in a first person mode, such as in the early ground breaking game DOOM™ that also introduced the concept of the "game engine" apart from the game itself. It is also well known to have character and animal objects, also called Non-player characters or NPCs, interact with subject within the game, and, in fact, the subject's interaction with such characters is often the entire point of a video game.

These well known components allow for creating a rich, realistic virtual environment for any imaginable scenario or environment for the subject to observe, and in many applications, interact with. The details of creating the virtual environment are not discussed in detail here, only briefly described in a manner sufficient to convey the key aspects of the present invention.

In the present invention the visual stimuli is in the form of virtual environment in which the subject will observe and typically interact with often in a first person perspective. The visual stimuli is presented in a test session to the subject on a display device including an eye tracking sub-system that can effectively track the subjects gaze direction and focus on the display device throughout the test session. The eye tracking system can be separate from the display monitor provided that the eye tracking system can record the eye tracking data as well as timing signals sufficient to synchronize the eye tracking data with the displayed session during subsequent evaluation with the attention tracking skins 30 of the present invention.

As discussed above a number of suitable eyetracking systems are available. The Tobii T/X™ series of eye trackers from Tobii Technology AB, provide an integrated display or monitor and eye tracking system that is well suited for the present invention. This eye tracker and monitor allows the eye tracked data to be accurately collected and integrated or synchronized with the session video throughout a session such that the gaze position on the monitor is known for each time period throughout the test session. It is the key feature of the present invention to easily map or assign this data to objects 10 of interest within the visual stimuli that has been presented in the session.

A critical feature of the present invention is that the objects 10 of interest can be differentiated from the remaining portions of the virtual environment through use of attention tracking skins 30 or unique colored wire frames 14. For example, unique colors may be assigned to the mesh frame and/or an eye tracking skin 30 of each object 10 of interest whereby the system can evaluate the obtained eye tracking data and assign attention data to specific objects 10 of interest resulting in object specific attention data. Specifically the system can evaluate the eye tracking data to determine where the focus is on the monitor and then review the color of the polygon 12 frame and/or the skin 30 at that location.

The unique colors will identify the objects of interest and the gaze data can then be associated with the appropriate objects 10 in an easy manner.

For example in a baseball batting scenario designed for pitch recognition or the like, the model 10 of the baseball in the simulation (either the frame or the skin or both) can be re-assigned the color blue as a eye tracking skin 30 and everything else (all other object skins in the environment) re-assigned to black for post session processing. The subject's session can then be "rerun" after the original session with the reassigned colors and skins 30 applied. This rerun of the data can occur at an accelerated speed so long as the playback frames are time synchronized with the stream of eye tracking data. The system will compare the color of the polygon 12 that is the focus of the gaze at each gaze data point and if it is blue the system will designate that the subject's focus was on the ball 10 for the given data point. To expand upon this example, the pitcher, the fielders and other base runners in the batting simulation may also be objects 10 of interest and each assigned unique colors so the system can designate the amount of attention data applied to each in a similar processing step. It should be clear that this processing, as described, may be a post processing procedure accomplished after the session has been accomplished. Further it should be apparent that the session can be re-run with different designations, as the researchers see fit. For example the researcher may go back and create a new skin 30 for the pitcher, or merely the pitchers throwing hand.

An object 10, such as the pitcher, may be divided into sub-objects 323 or object parts 32 (throwing hand, glove hand, feet, head), with each object part provided with a unique color designation to provide a breakdown of where on an object 10 a subject was concentrating.

The focal point of the gaze may not be a single polygon 12 but instead is more likely to be a focus range, or area of focus, such as a given diameter. This may be an adjustable parameter and accounts for "fovial dropoff". The system may attribute the attention data to all objects within the focus area for the given data point. Alternatively the focus area may have decreasing focus values toward the edges, in that objects near the center of the focus area are given an attention value of one and those near the edges are at or close to zero. This is referenced as an acuity weighting. The focus area may be non-circular as well, if desired. Various obvious strategies can be applied to optimize the acuity weighting, e.g. fractional proportion of colored pixels assigned to each object within the focus range vs "winner take all" whereby the object with the largest proportion of colored pixels within the focus range is assigned full value and others are assigned no value.

In one non-limiting embodiment of the present invention the second skin 30 of an object 10 of interest may be formed as a wash or range or gradient 34 of a given color from one end of the object 10 to the other as shown in FIG. 7C. For example, an automobile that is an object 10 of interest in a scenario may be provided with a second eye tracking skin 30 that has a continuously changing, gradient 34, shade of blue from the front of the car to the back of the car. With this "gradient" skin 30 the system can assign the eye tracking data to the car and specific sections (front to back) of the car as each different shade is a unique identifier. It should be apparent that the system has no difficulty is accurately distinguishing two shades that are only minutely different from each other.

Alternatively, the second skin 30 of an object 10 of interest may be formed as a combination of two or three colors with each color being a wash or range, or gradient 34 and 36, of a given color from one end of the object to the other in a given direction and wherein the directions for each color wash are angled with respect to each other. In the automobile example, shades of blue are used from front to back, yellow from top to bottom, and red from side to side. In this manner each particular location of the automobile will have a designated color that is set by particular combinations of red, blue and yellow within the range of each color. The level of uniqueness is determined only by the variation of colors that the system can distinguish.

In one non-limiting embodiment of the present invention the objects 10 of interest are assigned metadata that allows for sorting and categorizing the resulting object attention data. Metadata is data associated with an object in the virtual environment that is not part of the display parameters for rendering the object. For examples, non-player characters can be categorized by race, gender, clothing style, hair color, personality (e.g. smiling, happy, aggressive), height, weight, appearance, or any characteristic that the user deems helpful. The objects of interest can then be sorted accordingly.

For example, the user may desire the breakdown of attention data associated with females vs males NPC or short vs tall NPC or moving vs stationary objects within the session. The attachment of metadata is merely an additional tool for researchers to easily parse and accumulate robust attentional data sets. As with the second skin analysis, the metadata can be added in post processing as it does not effect the session from the subjects perspective.

In one non-limiting embodiment of the present invention the evaluation of the obtained eye tracking data and the assigning of attention data to specific objects 10 of interest that results in object specific attention data is obtained during the session. In other words the processing of the attention data is performed during the session itself. This analysis requires the designations of objects 10 of interest, at least originally to be made prior to the session. In this embodiment the designations of the objects 10 of interest may be through unique color identification of the frame 14 rather than the skin 20. In this manner a unique identifier is on the object 10 but the object 10, from the subjects view, does not look any different. The system, however, will identify that the focus is on a "blue" colored frame 14, for example, and identify the gaze with the "blue framed" object 10 of interest. This would be real time object based attention tracking in the virtual environment.

The real time object based attention tracking in the virtual environment allows for the virtual environment to be modified in accordance with the observed data. For example if the "yellow" framed objects 10 of interest are receiving less attention than a set threshold, additional "yellow" framed objects are presented in the ongoing session. As a representative example, if stop signs 10 in a driving tutorial are not receiving a predetermined threshold, then more stop signs 10 may appear later. In a gaming environment, consider a football simulation, if the subject, playing offense, fails to observe the safety 10 crowding the line before the safety blitz, then the game intelligence will call more safety blitzes to run against the subject later in the game (possibly regardless whether the initial safety blitz was successful). The real time processing will allow the object based attention tracking feature of the present invention provide feedback for the subsequent virtual environment that is presented to the subject.

The present invention provides a virtual world with the ability to control the texture/skin 30 or frame of the objects of interest therein that is run for the subject in a manner to obtain eye tracking data. The invention integrates the eye tracking data, that can operate at, at least, 50 hz, onto the objects 10 of interest by allowing the system to process, either real time or through post processing, the eye tracking data with the differentiated objects 10 of interest.

The present invention provides a tool that has a number of applications. The advertising uses of the present invention may be considered as an expansion of the advertising uses of eye tracking with static images. For example, instead of examining how potential customers view static images of a product, a realistic three dimensional virtual representation of the proposed new product concept can be developed in an ecologically valid virtual environment that can track how the subjects view the product in an interactive environment. For example what do they look at as they pick up the product and when the use the product. The subjects can, for example, drive new proposed cars. This is advantages from a human factors analysis and product evaluation analysis for advertising or product development.

Product placement can be reviewed with the present invention by having subjects walk through, for example, a virtual store or aisle of a store with product placement including competitor products, and allow for subjects to pull the product off of the shelf. This is far superior than the static image gaze path review of the store shelf.

Fashion design and clothing design represent another illustrative example of the present invention where a model of the cloths and the simulated human models modeling the clothing can be created virtually to better review attention data. In other words are the cloths attracting the attention or is it the models themselves that are garnering the attention? Further, what aspects of the clothing is attracting the attention.

As a medical example of the application of the present invention the patients gaze at a video image presented to the patient in an fmri environment can be accurately tracked and utilized in real time to assist the patient.

The research applications of the present invention are limitless. For example, virtual environments can be created to easily, accurately and objectively obtain drug evaluations for new drugs (and old drugs). Currently new drugs in clinical trials obtain a large variety of subjective data asking patients how they feel, did they observe any adverse effects, and the like. The present invention allows for testing particular drug effects for activities of daily living (ADLs). Note again that eye movements reflect the human thought process, consequently the attention tracking of the present invention can be used to objectively view how certain drugs may affect the human thought process.

The present invention can be used for bio-feedback device as described above in connection with the virtual simulation to held drive the simulation itself. This feedback is not limited to gaming, but is useful for research and training aspects of the invention. Attention tracking can be combined with other physical parameters, such as pupil size changes, to further evaluate what was associated with the gaze data. For example a surprise would be indicated by both the attention data and pupil size.

The present invention is well suited for training exercises of almost any type, particularly for scenarios that would be dangerous or impractical for real life processes. For example, training police officers to safely conduct a traffic stop, safely take persons into custody, drive defensively, observe and evaluate threats can all be particularly useful applications of the present invention with the appropriate virtual environment/scenarios.

The present invention is well suited for testing as well as training in a greater manner than existing testing simulators. For example in landing a plane the attention data can better explain failures rather than merely failing the test. As another example, in testing drivers, the test can see whether the new drivers are actually looking in the rear view mirror before changing lanes.

Although the present invention has been described with particularity herein, the scope of the present invention is not limited to the specific embodiment disclosed. It will be apparent to those of ordinary skill in the art that various modifications may be made to the present invention without departing from the spirit and scope thereof.

What is claimed is:

1. An operational method for object based attention tracking in a virtual environment comprising the steps of:
   supplying visual stimuli to at least one person in the form of a virtual environment in which at least the objects of interest have a three dimensional wire frame of that is surrounded with a skin, wherein the visual stimuli is presented in a session to the person on a display device;
   tracking the persons gaze direction and focus on the display device throughout at least a portion of the session with an eye tracking sub-system;
   assigning unique identifiers to the models of the objects of interest;
   evaluating the obtained eye tracking data and assigning attention data to specific objects of interest resulting in object specific attention data.

2. The operational method for object based attention tracking in a virtual environment according to claim 1 further including the step of applying a first realistic skin that is provided on the objects throughout the person's session; and applying a second eye tracking skin that is applied to the objects of interest before the session data is evaluated.

3. The operational method for object based attention tracking in a virtual environment according to claim 2 wherein the second skin of at least one object is divided into sub-objects.

4. The operational method for object based attention tracking in a virtual environment according to claim 3 wherein each object part provided with a unique color designation.

5. The operational method for object based attention tracking in a virtual environment according to claim 2 wherein the second skin of at least one object is formed as a gradient of a given color from one end of the object to the other.

6. The operational method for object based attention tracking in a virtual environment according to claim 2 further including the step of assigning metadata to the objects of interest that allows for sorting and categorizing the resulting object attention data.

7. The operational method for object based attention tracking in a virtual environment according to claim 2 wherein the evaluation of the obtained eye tracking data and the assigning of attention data to specific objects of interest that results in object specific attention data is obtained during the session.

8. The operational method for object based attention tracking in a virtual environment according to claim 2 wherein the evaluation of the obtained eye tracking data and the assigning of attention data to specific objects of interest that results in object specific attention data is obtained following the session in post session processing.

9. The operational method for object based attention tracking in a virtual environment according to claim 1 further including the step of applying a first realistic skin that is provided on the objects throughout the person's session.

10. The operational method for object based attention tracking in a virtual environment according to claim 9 wherein the unique identifiers are represented by unique colors and wherein unique colors are assigned to the mesh frame.

11. The operational method for object based attention tracking in a virtual environment according to claim 10 wherein the evaluation of the obtained eye tracking data and the assigning of attention data to specific objects of interest that results in object specific attention data is obtained during the person's session.

12. The operational method for object based attention tracking in a virtual environment according to claim 10 further including the step of assigning metadata to the objects of interest that allows for sorting and categorizing the resulting object attention data.

13. The operational method for object based attention tracking in a virtual environment according to claim 9 wherein the evaluation of the obtained eye tracking data and the assigning of attention data to specific objects of interest that results in object specific attention data is obtained during the person's session.

14. The operational method for object based attention tracking in a virtual environment according to claim 9 wherein the evaluation of the obtained eye tracking data and the assigning of attention data to specific objects of interest that results in object specific attention data is obtained following the session in post session processing.

15. The operational method for object based attention tracking in a virtual environment according to claim 9 further including the step of assigning metadata to the objects of interest that allows for sorting and categorizing the resulting object attention data.

16. An operational method for object based attention tracking in a virtual environment comprising the steps of:
   supplying visual stimuli to at least one person in the form of a virtual environment in which at least the objects of interest have a three dimensional wire frame of that is surrounded with a skin, wherein the visual stimuli is presented in a session to the person on a display device;
   tracking the persons gaze direction and focus on the display device throughout at least a portion of the session with an eye tracking sub-system;
   assigning unique identifiers to the models of the objects of interest;
   evaluating the obtained eye tracking data and assigning attention data to specific objects of interest resulting in object specific attention data further including the step of applying a first realistic skin that is provided on the objects throughout the person's session; and applying a second eye tracking skin that is applied to the objects of interest before the session data is evaluated wherein the second skin of at least one object is formed as a combination of at least two colors with each color being a gradient of a given color from one end of the object to the other in a given direction and wherein the directions for each color gradient are angled with respect to each other.

17. An operational method for object based attention tracking in a virtual environment comprising the steps of supplying visual stimuli to at least one person in the form of a virtual environment in which at least the objects of interest have a three dimensional wire frame that is surrounded with at least one skin; wherein the visual stimuli is presented in a session to each person on a display device including an eye tracking sub-system that can effectively track the person's gaze direction and focus on the display device throughout at least a portion of the session; wherein unique identifiers are assigned to at least one of the wire frame and an eye tracking skin of each object of interest whereby the system can evaluate the obtained eye tracking data and assign attention data to specific objects of interest resulting in object specific attention data.

18. The operational method for object based attention tracking in a virtual environment according to claim 17 wherein the evaluation of the obtained eye tracking data and the assigning of attention data to specific objects of interest that results in object specific attention data is obtained during the session.

19. The operational method for object based attention tracking in a virtual environment according to claim 17 wherein the evaluation of the obtained eye tracking data and the assigning of attention data to specific objects of interest that results in object specific attention data is obtained following the session in post session processing.

20. The operational method for object based attention tracking in a virtual environment according to claim 17 further including the step of assigning metadata to the objects of interest that allows for sorting and categorizing the resulting object attention data.

* * * * *